United States Patent [19]

Williams et al.

[11] Patent Number: 4,666,439
[45] Date of Patent: May 19, 1987

[54] HYGIENIC ABSORBENT PADS

[75] Inventors: Pamela J. Williams, Solihull; John G. B. Howes, Hertford Heath, both of United Kingdom

[73] Assignee: Smith & Nephew Associated Companies Limited, England

[21] Appl. No.: 744,808

[22] Filed: Jun. 14, 1985

[30] Foreign Application Priority Data

Jun. 16, 1984 [GB] United Kingdom ............... 8415428
Mar. 12, 1985 [GB] United Kingdom ............... 8506299

[51] Int. Cl.[4] .......................................... A61F 13/16
[52] U.S. Cl. ................................................. 604/368
[58] Field of Search ............... 604/364, 368, 372, 378, 604/385

[56] References Cited

U.S. PATENT DOCUMENTS

| 3,344,789 | 10/1967 | Arnold et al. | 604/368 |
| 4,200,103 | 4/1980 | Black et al. | 604/372 |
| 4,212,302 | 6/1980 | Karami | 604/368 |
| 4,333,462 | 6/1982 | Holtman et al. | 604/368 |
| 4,410,324 | 10/1983 | Sabee | 604/368 |
| 4,596,569 | 6/1986 | Iskra | 604/368 |

Primary Examiner—John D. Yasko
Attorney, Agent, or Firm—Jacobs & Jacobs

[57] ABSTRACT

A hygienic absorbent pad is described which comprises an elongate absorbent core, a liquid pervious sheet over the front face of the absorbent core and a liquid absorbent core, which barrier sheet has longitudinal edge portions which cover the longitudinal sides of the absorbent, which longitudinal edge portions have a layer in contact with a surface thereof of a water absorbing polymer such as a hydrophilic polyurethane which is capable of inhibiting leakage of body fluids from the front surface of the absorbent pad to the sides thereof.

9 Claims, 3 Drawing Figures

HYGIENIC ABSORBENT PADS

The invention relates to hygienic absorbent pads, materials therefor and method of manufacture.

Conventional hygienic absorbent pads such as sanitary towels, diapers, incontinence pads and the like usually comprise an elongate absorbent core, a liquid pervious sheet over the front face of the absorbent core and a liquid impervious barrier sheet over the back face of the absorbent core. The absorbent core will normally have one or more layers of absorbent material such as wood pulp, cellulosic fibres, fauze, tissue or synthetic polymer foam which may be contained within for example a tissue wrapper. The liquid pervious sheet over the front face of the absorbent-core is normally a soft fabric for example soft non-woven fabric which is suitable for contact with the body. The liquid impervious barrier sheet over the back face of the absorbent core is normally a thin flexible plastics film, such as 0.10 to 0.04 mm thick polyethylene film. These hygienic absorbent pads may have an attachment means, for example adhesive strips on the back face of the pad, which allow the pad to be attached to a support garment or belt used to position the pad against the body. Conventional hygienic absorbent pads are intended to be used until the pad becomes saturated with absorbed fluid. However in practice premature leakage of body fluid from the pad often occurs before saturation of the pad is reached. Premature leakage of body fluids from the pad can cause staining of the support or associated garments and therefore frequent changing of the pad is often necessary to prevent such staining. It is believed that premature leakage is caused by exuding body fluid contacting and temporarily saturating the top layers of absorbent material at a central area of the pad, which then causes the body fluid to migrate by wicking or flowing across the front surface of the pad from the central area to the side edges of pad adjacent thereto before it has penetrated into main bulk of the pad. In order to overcome this problem hygienic absorbent pads and in particular sanitary towels have been provided with a barrier sheet which is wider than the back face of the absorbent core and which has longitudinal edge portions which cover the longitudinal sides and preferably also the side margins of the front face at the absorbent core. The liquid pervious sheet of such pads usually envelopes the absorbent core and the liquid impervious barrier sheet to prevent contact of the barrier sheet with the body. A sanitary towel of this construction is disclosed in United Kingdom application No. GB 2019727B. Although the use of a barrier sheet of the type disclosed in this patent can prevent premature leakage from the side edges of the pad it will not prevent body fluid wicking for example along the liquid pervious cover or flowing from the front surface of the pad over the edge portions of the barrier sheet and to the sides of the pad. United Kingdom application No. GB 2019727B further discloses a sanitary towel which has two menstrual fluid barrier seal lines which seal the liquid pervious envelope or wrapper to the longitudinal edge portions of the barrier sheet. These seal lines inhibit wicking of the fluid along the wrapper over the edges of the barrier sheet to the sides of the towel. These seal lines, however, would not act as a barrier to body fluids flowing over the edges of the barrier sheet. Hygienic absorbent pads have now been discovered which inhibit premature leakage and in a preferred form also inhibit body fluids being transmitted over the edge of the barrier sheet.

Accordingly the present invention provides a hygienic absorbent pad which comprises an elongate absorbent core, a liquid pervious sheet over the front face of the absorbent core and a liquid impervious barrier sheet over the back face of the absorbent core, which barrier sheet has longitudinal edge portions which cover the longitudinal sides of the absorbent core characterised in that said longitudinal edge portions of the barrier sheet have a layer in contact with a surface thereof of a water absorbing polymer which is capable of inhibiting leakage of body fluids from the front surface of the absorbent pad to the sides thereof.

In preferred embodiments of the invention the longitudinal edge portions of the barrier sheet also cover the side margins at the front face of the absorbent core and the liquid pervious sheet surrounds the absorbent cover and the barrier sheet.

The hygienic absorbent pads of the invention include sanitary towels, diapers and incontinence pads. The invention is particularly suitable for use in sanitary towels where the advantages produced are most important.

The longitudinal edge portions of the barrier sheet used in the invention have a layer of water absorbing polymer in contact with a surface thereof. The layer of water absorbing polymer can be a layer intimately on a surface of the longitudinal edge portions of the barrier sheet, for example, a coating.

Thus in one favoured aspect the invention provides a sanitary towel which comprises an elongate absorbent core, a liquid impervious barrier sheet over the back face of the absorbent core and a liquid pervious sheet which surrounds the absorbent core and the barrier sheet which barrier sheet has longitudinal edge portions which cover the longitudinal sides of the absorbent core and the side margins at the front face thereof characterised in that said longitudinal edge portions of the barrier sheet have a layer on a surface thereof of a water absorbing polymer which is capable of inhibiting leakage of body fluids from the front surface of the absorbent pad to the sides thereof.

More favourably the layer of water absorbing polymer used in the invention can be on the parts of the inner surface of a liquid pervious sheet which contact the longitudinal edge portions of the barrier sheet.

Thus in another preferred aspect the invention provides a sanitary towel which comprises an elongate absorbent core, a liquid impervious barrier sheet over the back face of the absorbent core which barrier sheet has longitudinal edge protions which cover the longitudinal sides of the absorbent core and the side margins at the front face thereof and a liquid pervious sheet which surrounds the absorbent core and the barrier sheet so that parts of the inner surface of the liquid pervious sheet contact the longitudinal edge portions of the barrier sheet characterised in that said parts of the inner surface of the liquid pervious sheet have a layer thereon of a water absorbing polymer which is capable of inhibiting leakage of body fluids from the front surface of the absorbent pad to the sides thereof.

A layer of water absorbing polymer can be provided on both the longitudinal edge portions of the barrier sheet and the parts of the inner surface of the liquid pervious sheet which contact these portions. If desired layers can be bonded together for example under heat and pressure to form a barrier to fluid leaking between the barrier and liquid pervious sheets of a hygienic absorbent pad of the invention. Alternatively a similar fluid barrier can be formed by bonding, for example heat sealing, a layer of water absorbent polymer on the surface of one of the barrier or liquid pervious sheets to the surface of the other sheet. However such bonding of the pervious and barrier sheets together is not preferred since it can be disadvantageous in that the resulting product can be less comfortable (possibly since the layers are prevented from sliding over one another) and can employ more polymer than would be otherwise required. From the foregoing it will be understood that in a favoured aspect this invention provided a product in which the water absorbent polymer is disposed in a manner which does not lead to the sealing together of the barrier and pervious layers.

It is possible to maintain the barrier and the pervious layers in place with respect to each other by sealing at the back of the pad, for example by using adhesive lines on the garmetn facing surface of a sanitary towel. This arrangement allows for a slight relative movement of the two layers at the body facing surface of the pad which can lead to greater comfort.

The water absorbing polymer layer in contact with the longitudinal edge portions of the barrier sheet of a pad of the invention will make contact with and absorb body fluid passing over these edge portions from the front face of the pad, for exmaple body fluid flowing or wicking across the liquid pervious sheet on the front surface of the pad, and thus will inhibit leakage of body fluid to the sides of the pad. The inhibition of such premature leakage of body fluid from the pad can prevent staining of the wearer's garment and may also increase the useful absorbent capacity of the absorbent pad.

The water absorbing polymers used in this specification will of course be polymers which absorb water on contact therewith but which are water insoluble. These water absorbing polymers are commonly known as hydrophilic polymers.

Hydrophilic polymers for use in the invention suitably have a water content when hydrated of at least 20%, more suitably of at least 40%, desirably of at least 70% and preferably of at least 80% (weight for weight). These hydrophilic polymers will normally have a water content when hydrated of not greater than 97% and preferably have a water content when hydrated of not greater than 95% by weight.

Thus favoured hydrophilic polymers have a water content when hydrated of 40 to 97% by weight, desirably have a water content when hydrated of 70 to 95% by weight and preferably have a water content when hydrated of 80 to 95% by weight.

% Water content of the hydrated polymer can be calculated from the weight of water in the polymer after it has been immersed in water at 20° C. % Water content can be determined by weighing a dry sample of the polymer, allowing it to equilibrate in water and reweighing the hydrated polymer after wiping off external moisture.

The hydrophilic polymers for use in the invention can be cross-linked or linear polymers. Linear hydrophilic polymers have been found to be applicable as thin film to a support such as the barrier or pervious layer by a simple solution or hot melt coating or extrusion process and are therefore it is preferred hydrophilic polymers for use in the invention. Suitable linear hydrophilic polymers include linear hydrophilic polyurethanes, linear hydrophilic acrylic polymers, hydrophilic polyether ester polyamide polymers and polyvinyl alcohols with a degree of hydrolysis of 97 to 99.5%.

An apt polyether ester polyamide polymer is a thermoplastic polymer which has a water content when hydrated of 54.3% known as Pebax 4011 RN 010 available from ATO Chemical Products (UK) Limited.

An apt polyvinyl alcohol has a degree of hydrolysis of 98.5 to 99.2% and a molecular weight of 80,000 known as Gohsenol N300 available from Nippon Gohsei.

Preferred linear hydrophilic polymers are linear polyether polyurethanes. Favoured water absorbing polymers for use in the invention are linear polyether polyurethanes which have a water content when hydrated of at least 20%, more suitably at least 40%, desirably at least 70% and preferably at least 80% (weight for weight). Preferably such materials contain 40% to 95% water when hydrated.

The liquid pervious sheet and liquid impervious barrier sheet components of hygienic absorbent pads of the invention can be conventional materials of the art as mentioned hereinbefore, which have been adapted for use in the invention.

The water absorbing polymer layer on the longitudinal edge portions of the barrier sheet used in the invention can be on the inner surface, that is the surface of the barrier sheet which is in contact with the absorbent core, or the outer surface, that is the surface of the barrier sheet which is not in contact with the absorbent core. It is preferred, however, that the water absorbing polymer layer is on the outer surface of the longitudinal edge portions of the barrier sheet. In such a position the water absorbing polymer will make good contact with and absorb body fluids leaking to the sides of the absorbent pad.

The water absorbing polymer layer can be on the part of the longitudinal edge portions of the barrier sheet which cover the longitudinal sides of the absorbent core or on the part of the edge portions of the barrier sheet which cover the side margins at the front face of the absorbent core or if convenient over both parts of said edge portions of the barrier sheet. If the water absorbing polymer is on the inner surface of the barrier sheet it is most aptly on part of the edge portions thereof which cover the side margins at the front face of the absorbent core.

The water absorbing polymer layer on the longitudinal edge portions of the barrier sheet will be in a form for example a line or strip, which will provide a barrier to body fluids leaking from the front face of the pad over the sides thereof. The water absorbing polymer layer is preferably in the form of a continuous strip. In preferred embodiments of the invention one or more such continuous strips can be provided on longitudinal edge portions of the barrier sheet. The strips may extend along part of the longitudinal edge portions for example the part of edge portions which is adjacent to the central area of the pad. It is preferred, however, that the strips extend along the whole length of longitudinal edge portions of the barrier sheet which covers the absorbent core.

The strips of water absorbing polymer may be at or somewhat away from the edge of the barrier sheet. It is preferred, however, that the strips of water absorbent polymer are coterminous with the longitudinal edges of the barrier sheet. This aids in contact of the polymer with body fluid leaking from the front face of the pad to the sides.

If the layer of water absorbing polymer on parts of the surface of the liquid pervious sheet of the invention will normally be in the form of a line or strip as hereinbefore described in relation to the barrier sheet of the invention. Such lines or strips of water absorbing polymer will preferably be on the surface of the liquid pervious sheet which is adapted to face the barrier sheet and will preferably be located in a position on the surface which in use will contact the outer surface of the longitudinal edge portions of the barrier sheet. The liquid pervious sheet can suitably have two or more lines or strips. Preferred liquid pervious sheets of the invention, however, have a pair of lines or strips of water absorbing polymer.

These pairs of lines or strips will normally be straight parallel lines or strips which extend in the longitudinal direction of the sheet and are preferably located on at least the central region of the sheet. The length of the lines or strips can be adapted to contact in use part of the longitudinal edge portions of the barrier sheet for example that part of longitudinal edge portions which are adjacent to the central area of the pad. It is preferred, however, that the length of lines or strips is adapted to contact in use the whole length of the longitudinal edge portions of the barrier sheet.

The water absorbing polymer layer if on the liquid pervious sheet is preferably in the form of two or more a continuous strip. The distance between such strips on the liquid pervious sheet can be adapted so that in use the strips are inset from, coterminous with or preferably overlap the longitudinal edges of the barrier sheet. This aids in contact of the water absorbing polymer with body fluid leaking from the front face of the pad to the sides of the pad.

The distance between the edges of a pair of strips or lines on a liquid pervious sheet of the invention can suitably be 40 to 70 mm and can preferably be 50 to 60 mm.

Suitable strips of water absorbing polymer for use on the barrier and liquid pervious sheets of sanitary towels have a width of 2 to 15 mm, desirably a width of 3 to 10 mm and preferably a width of 4 to 7 mm. The strip layers of water absorbing polymer are preferably thin film layers. These strip film layers can suitably have a thickness of 0.010 to 0.1 mm and preferably a thickness of 0.025 to 0.05 mm. Similarly these film layers can suitably have a weight per unit area of 10 to 80 g/m$^2$ and preferably a weight per unit area of 25 to 50 g/m$^2$.

Where herein it is stated that the layer of water absorbing polymer is and surface, it should not be construed as implying that the polymer cannot penetrate into a surface where that surface is porous, for example where the previous layer is a non-woven fabric.

The absorbent core used in the hygienic pad of the invention can comprsie conventional materials of the art for example as mentioned hereinbefore. The hygienic absorbent pad can have adhesive, for example a pair of adhesive strips, on its back face covered by a release protector strip or strips which can be removed to allow the pad in use to be adhered to a supporting garment.

In a preferred hygienic absorbent pad of the invention in which the liquid pervious sheet surrounds the absorbent core, the adhesive on the back face of the pad penetrates the liquid pervious sheet to adhere overlapped portions thereof and also to adhere the sheet to the backing sheet.

In yet a further aspect the invention provides a method of forming a hygienic absorbent pad of the invention which comprises covering the front face of an elongate absorbent core with a liquid pervious sheet and covering the back face and longitudinal sides of the absorbent core with a liquid impervious barrier sheet so that the longitudinal edge portions of the barrier sheet cover the longitudinal sides of the absorbent core characerised in that said longitudinal edge portions of the barrier sheet have a layer in contact with a surface thereof a water absorbing polymer which is capable of inhibiting leakage of body fluids from the front surface of the absorbent pad to the sides thereof.

In the method of the invention it is preferred that longitudinal edge portions of the barrier sheet also cover the side margins at the front face of the absorbent core and the liquid pervious sheet surrounds the absorbent core and the barrier sheet.

The materials used in the method of the invention can be the same as hereinbefore described in relation to hygienic absorbent pads of the invention.

The layer of water absorbent polymer which is preferably in the form of continuous strips applied to the barrier sheet or liquid pervious sheet by any suitable process which includes solvent coating, hot melt coating or extrusion coating the layer directly onto the sheet or forming the layer separately and bonding the formed layer to the sheet for example by a process which employs heat and pressure such as heat sealing.

Preferred water absorbing polymers for use in the invention are linear hydrophilic polyether polyurethanes.

The barrier sheet typically a low density polyethylene film can be provided on its longitudinal edge portions with a continuous strip and layer of hydrophilic thermoplastic polymer by a conventional extrusion coating process using a filament or tape die provided with a row of spaced apart holes or slots.

The liquid pervious sheet, which is typically a nonwoven fabric, can be provided on parts of its surface intended to contact the longitudinal edge portions of the barrier sheet with a layer of hydrophilic polymer, for example in the form of a pair of parallel straight strips located at a central region of the sheet by a similar coating or extrusion coating process as used hereinbefore for the barrier sheets.

The pads may be assembled in conventional manner.

The invention is illustrated by reference to the following drawing.

Figure 1:
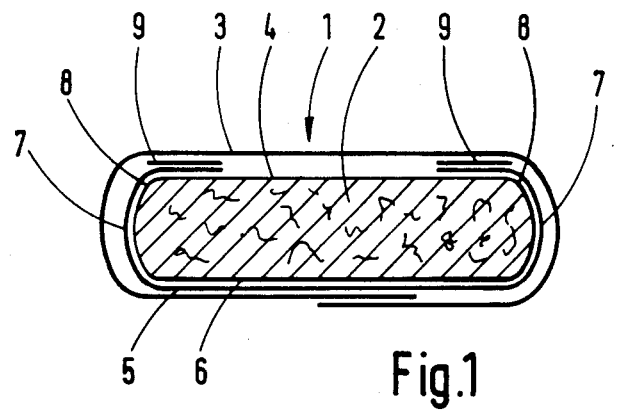
FIG. 1 is a schematic cross-sectional view of a sanitary towel of the invention.

FIG. 1 shows a sanitary towel (1) comprising a generally elongate absorbent core (2) which has a liquid pervious sheet (3) over its front face (4) and a liquid impervious barrier sheet (5) over its back face (6). The liquid pervious sheet (3) shown in FIG. 1 surrounds the absorbent core (2) and the liquid impervious barrier sheet (5). The liquid impervious barrier sheet (5) has edge portions (7) which cover the longitudinal sides and the side margins (8) at the front face of the absorbent core (2). The outer surface of the edge portions (7) of the barrier sheet (5) which cover the side margins at the front face of the absorbent core have a film layer (9) of water absorbing polymer.

Figure 2:
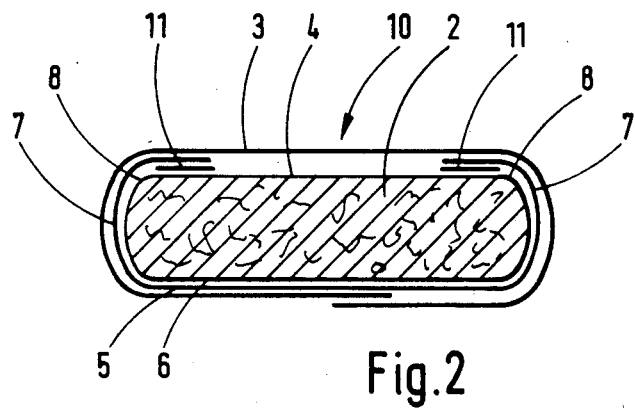
FIG. 2 is a schematic cross-sectional view of another sanitary towel of the invention.

FIG. 2 shows another sanitary towel (10) which is similar to sheet of FIG. 1 except that the layer (11) of water absorbing polymer is provided on the inner surface of edge portions (7) of the barrier sheet (5) which cover the side margins at the front face of the absorbent core (2).

Figure 3:
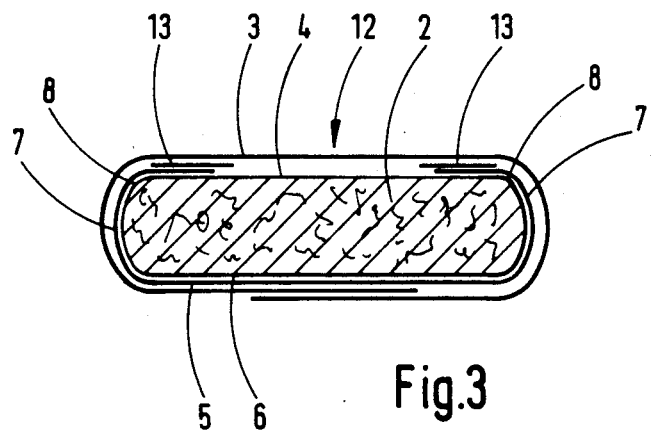
FIG. 3 is a schematic cross-sectional view of yet another sanitary towel of the invention.

FIG. 3 shows a sanitary towel (12) similar to that of FIG. 1 except that the layer of water absorbing polymer (13) is provided on the inner surface of parts of the liquid pervious sheet (3) which contact the outer surface of longitudinal edge portions (7) of barrier sheet (5) which cover the side margins at front face of the absorbent core (2).

The sanitary towels of FIGS. 1 to 3 when positioned against the perineal area of the body can absorb body fluid exudates which pass through the liquid pervious sheet (3) into the absorbent core (2). Any body fluid which flows across the front face of the towel (4) towards the side edges thereof will make contact with and be absorbed by the water absorbing polymer layer (9, 11, 13) in contact with the edge portions (7) of the barrier sheet (5). The water absorbing polymer layers therefore will inhibit leakage of body fluids from the front surface of the sanitary towel to the sides thereof and thus prevent staining of the wearer's garment. Furthermore the hygienic absorbent pads of the type shown in FIG. 1 and 3 in which the water absorbing polymer is in contact with the outer surface of barrier sheet have the advantage that any body fluid which exudes directly on to the edge portions (7) which cover the side margins at the front face of the core, which can occur for example when the pad is distorted in use, will be absorbed by the polymer before any staining of the wearer's garment occurs.

Apt linear hydrophilic polyether polyurethanes for use in the invention have a water content when hydrated of 40% to 95% by weight. Such linear polyurethanes can be derived from polyethylene glycol, a chain extender selected from a group consisting of water, aliphatic diols and aliphatic diamines and di-isocyanates.

Suitable polyethylene glycols for forming the linear hydrophilic polyether polyurethanes used in the invention have a molecular weight of 1000 to 10000 and preferably a molecular weight of 3000 to 9000, for example Breox 6000 and 8000 available from B.P. Chemicals. Small quantities of polyethyleneoxide-polypropylene copolymers may be used to replace minor properties of the polyethylene glycols.

Suitable aliphatic diols include ethane diol, propane diol and 1,4 butane diol.

Suitable di-isocyanates for forming the linear hydrophilic polyether polyurethanes used in the invention include aromatic di-isocyanates such as 4–4' diphenyl methane di-isocyanate and toluene di-isocyanate, and aliphatic di-isocyanates such as 1,6-hexamethylene di-isocyanate and 4,4'-dicyclo hexyl methane di-isocyanate. Favoured di-isocyanates for use in the invention are aliphatic di-isocyanates of which 4,4'-dicyclohexyl methane di-isocyanates is preferred (for example Desmodur W available from Bayer). Hydrophilic polyurethanes having a water content of 40% to 67% when hydrated are disclosed in United Kingdom GB 2093190A and in C. T. Chen et al., J. Appl. Polymer Science (1972) Vol 16 p 2105–2114 but no suggestion was made therein that the quantity of hydrophilic component of the polymer should be increased thereby increasing the water content of the final hydrated polymer.

Apt linear hydrophilic polyether polyurethanes having a water content of 80% to 95% when hydrated can be derived from polyethylene glycol of molecular weight of 6000 to 10000, water and a di-isocyanate such an aliphatic diisocyanate for exmaple as 4,4'-dicyclohexyl methane diisocyanate in a molar ratio of about 1:4.2:2.6 (NCO/OH ration 0.5:1).

It has been found to be advantageous to have linear hydrophilic polyurethanes of highwater content which are thermoplastic and can be easily used to provide a water absorbent polymer layer for use in the invention by a non-solvent method. This in a further aspect the invention provides a linear hydrophilic polyurethane (suitable for use as a water absorbing polymer layer in hygienic absorbent pads of the invention) characterised in that the linear hydrophilic polyurethane is thermoplastic and has a water content when hydrated of 80% to 95% by weight.

Preferred thermoplastic linear hydrophilic polyurethanes for use in the invention are linear hydrophilic polyether polyurethanes. Such polyurethanes can be derived from (a) polyethylene glycol of molecular weight 5000 to 10000 (b) aliphatic diol (c) water and (d) a diisocyanate in which the molar ratio of (c) to (a) is suitably <1:1 and is preferably <0.5:1, the molar ratio of (a) to (b) plus (c) is suitably 1:2 to 2:1 and is preferably 1:1.5 to 1:1 and the molar ratio of (d) to (a) plus (b) plus (c) (NCO/OH ratio) is suitably 0.7:1 to 1:1 and is preferably 0.9:1 to 1:1.

Preferred aliphatic diols include ethane diol and 1,4 butane diol. Preferred di-isocyanates include 4,4'-dicyclohexylmethane di-isocyanate and 4,4'methylene bis di-isocyanate.

Favoured thermoplastic hydrophilic polyurethanes of the invention have a water content of approximately 90 to 92% by weight and are derived from polyethylene glycol of molecular weight 6000 to 9000, 1,4 butane diol, water and 4,4'-dicyclohexyl methane di-isocyanate in a molar ratio of 1:0.5:0.5:1.8 or 1:1:0.3:2.07 respectively. These favoured thermoplastic linear polyether hydrophilic polyurethanes can be extrusion coated as a layer on to a barrier film or a liquid pervious sheet used in the hygienic absorbent pads of the invention.

Linear hydrophilic polyether polyurethanes used in the invention can be made by melting the polyethylene glycol in a suitable container. The chain extender, the antioxidant if necessary, di-isocyanate and catalyst are then mixed in that order with the liquid polyethylene glycol by stirring. The mixture may then be transferred to a tray and allowed to polymerise in an oven for example at 90° C. for 2 to 3 hours. The chain extender can be water which is already present in the polyethylene glycol. A suitable catalyst is n di-butyl tin laurate known as catalyst T12. A suitable antioxidant is Irganox 1010.

The hydrophilic polyurethane once formed can be granulated in a conventional manner. The granulated polymer can be dissolved in a suitable solvent such as a 1:1 mixture of methylene chloride and ethyl alcohol (IMS) for use in a solvent coating process. Alternatively the granulated polymer if thermoplastic can be used in a hot melt coating or extrusion process.

The following Examples, illsutrate the invention.

EXAMPLE 1

Preparation of the hydrophilic polyurethane 45.25 g (0.005 moles) of polyethylene glycol of molecular weight 9050 containing 0.379 g (0.0211 moles) of water was added into a glass container and melted by heating to 70° C. 3.42 g (0.013 moles) of Desmodur W was added to the container and mixed by stirring. 0.09 g (0.2%) of catalyst T12 was then added and the mixture stirred for about 1 minute. The mixture was then poured into a mould and placed in an oven at 90° C. for two hours to complete the polymerisation. The polymer was then granulated and the granulated polymer dissolved in a 1:1 mixture of methylene chloride and ethyl alcohol (IMS) to form a solution containing 15% by weight of polymer.

The linear hydrophilic polyurethane was found to have a water content when hydrated of apprpximately 92% by weight.

The edge portions (5 mm wide) of a 90 mm wide flexible low density polyethylene film (0.030 mm thick) were coated by a conventional knife over flat bed coating head with the solution prepared above and dried in an oven at 70° C. The resultant film had 5 mm wide strip layer of hydrophylic polyurethane coated along its edge portions having a weight per unit area of 40 g/m².

An elongate core (180 mm long × 65 mm wide) consisting of wood pulp (300 g/m²) wrapped in a tissue wadding was placed on the coated barrier film as prepared above and the edge portions of the film folded around the longitudinal edges of the core to cover the side margins at the front surface of the core so that the coated polymer was on outer surface of the edge portions of the barrier film. The front surface of the absorbent core was then covered by carded thermally bonded polypropylene non-woven fabric strip which was folded around the bottom surface of the core to form an envelope. The overlapping margins of barrier film and the non-woven fabric at the ends of the absorbent core were then sealed by heat and pressure in a conventional manner and pressure sensitive adhesive strips provided at the bottom surface of the pad to form the pad of the invention.

Sanitary towels of the invention made according to Example 1 were submitted to user test on adult females in comparison with similar sanitary towels having a barrier film which was not coated with hydrophilic polyurethane.

It was found that out of a 37 sample sanitary towels of the invention used in the test only two showed slight leakage, whereas 20 of the 78 conventional sanitary towels used in the test showed severe to slight leakage.

EXAMPLE 2

Preparation of the thermoplastic linear hydrophilic polyurethane

Polyethylene glycol of mol weight 8360 (1 mole) was added to a glass container and melted by heating to a temperature of 70°. 1,4 Butane diol (0.5 mole) and Irganox 1010 (1.0% by wt) were dispersed into the mixture by stirring. Desmodur W (1.8 mole) was then added gradually and the mixture stirred gently until it was homogeneous. Catalyst T12 (0.2% by wt) was added with trays and placed in an oven at 90° C. for 2 hours to complete the polymerisation.

The polyethylene glycol used in this example was dried under vacuum at 70° C. to water content of 0.11% which is equivalent ot 0.5 mole of water.

The polymer when hydrated had a water content of 91.8% by weight.

It was found that the polymer could be extruded as a film (0.025 mm thick) using a die temperature of approximately 100° C. on to low density polyethylene film (0.03 mm) thick to form a coated film suitable for use as barrier film on absorbent pads of the invention.

EXAMPLE 3

Preparation of Sanitary Towel

The edge portions on one surface of 90 mm wide flexible low density corona discharge treated polyethylene film (0.030 mm thick) were extrusion coated with 5 mm wide strips (weight per unit area of 32 g/m²) of the polyurethane of Example 2 to provide a barrier film for use in a sanitary towel of the invention.

The strips of polyurethane were formed on the polyethylene film by extruding the polyurethane, using an extruder fitted with a two bead filament die, as two spaced apart filaments onto portions of the film inset 3 mm from the edges of the film which was then fed between the nip of two casting rollers (maintained at a temperature of 20° C.) to press the filaments into 5 mm wide strips.

The extruder used in this example was a Brabender Extrusiograph extruder (length to diameter screw ratio of 25:1) driven by a Brabender PLE 651 plasticorder. The two.bead filament die used had two circular die holes of 1mm diameter which were spaced 84 mm apart. The die was heated to a temperature of 105° C. during the extrusion process.

Sanitary towels were prepared in the same manner as the sanitary towels of Example 1 using the coated barrier film prepared above. The distance between the coated longitudinal edges of the barrier sheet at the front face of the absorbent pad was approximately 55 cm.

EXAMPLE 4

Preparation of Sanitary Towel

A 180 mm wide non woven fabric of thermally bonded carded polypropylene fibres (weight per unit area of 18 g/m²) was extrusion coated in the length direction of the fabric with a pair of parallel 5 mm wide strips (weight per unit area 36 g/m²) of the polyurethane of Example 3.

The coated strips were on a central region of the fabric and the distance between the inner edges of the coated strips was 56 mm.

The extrusion coating of the liquid pervious sheet was carried out in the same manner as the extrusion coating of the barrier film of Example 3 except that the two bead filament die had 1mm circular die holes which were spaced 60.5 mm apart, the die was heated to a temperature of 120° C. and the casting rollers were maintained at a temeprature of 15° C.

Sanitary towels were prepared in the same manner as the sanitary towels of Example 1 except that the pair of longitudinal strips of polyurethane on the inner surface of the liquid pervious fabric were positioned over longitudinal edge portions of the barrier film at the front face of the absorbent pad.

Demonstration Methods

Edge Leakage Test

The coated barrier film of Example 3 and the coated liquid pervious fabric of Example 4 were tested in comparison with similar uncoated materials in an edge leakage test as follows.

A rectangle of the barrier film (0.03 mm thick low density polyethylene 150 mm long, 90 mm wide) was mounted on a sloping surface (29% gradient) with a polymer coated edge of the film positioned at the bottom of the slope and facing outwards. The film was then covered by a similar size liquid pervious non-woven fabric with the polymer coated strip on its inner surface positioned over and adjacent to the longitudinal edge portion of the film. A coloured synthetic menstrual fluid (aqueous solution containing 1% by weight of sodium chloride coloured with a green dye) was dripped slowly onto the surface of the non-woven fabric at a central position thereof located 3.5 mm above the bottom edge of the film. The amount of fluid (mls) absorbed before leakage occurred at the bottom edge of the film was then measured. The results were as follows:

| Test No. | Combination Barrier film | Liquid pervious fabric | Amount of fluid absorbed before leakage (mls) 1 | 2 | 3 | Average |
|---|---|---|---|---|---|---|
| 1 | Coated film of Example 4 | Uncoated fabric | 0.8 | 1.0 | 1.0 | 0.9 |
| 2 | Uncoated film | Coated fabric of Example 5 | 1.0 | 1.0 | 0.8 | 0.9 |
| 3 | Uncoated film (Control) | Uncoated fabric | 0.5 | 0.4 | 0.3 | 0.4 |

(b) In order to demonstrate the suitability of certain water absorbent polymers for use in the invention, a layer of the polymer was formed as a 5 mm wide strip along a longitudinal edge portion of a typical barrier film (0.03 mm thick low density polyethylene film 150 mm long and 90 mm wide) and the barrier film tested in the edge leakage test described in (a). In this test the test barrier film was used in combination with an uncoated liquid pervious non-woven fabric. The test was carried out on a number of barrier films each provided with an edge strip layer of a different water absorbent polymer and on a comparison barrier film without such a layer. In order to provide the barrier film with an edge strip layer of polymer, the water absorbent polymer was first formed into an approximately 0.025 mm thick film by a conventional solvent or extrusion casting process, sprayed on one surface with a solution of a non-hydrophilic polyurethane to provide a heat sealable surface, cut into 5 mm wide strips and bonded by heat sealing at 80° C. to a longitudinal edge portion of a barrier film. The following results were obtained:

| Polymer layer on Barrier film | Weight g/m² | Amount of fluid absorbed before leakage (mls) |
|---|---|---|
| HPU 45 | 30 | 0.5 |
| HPU 90 (Ex. 3) | 30 | 0.5 |
| Gohsenol N 300 | 30 | 0.4 |
| PEBAX 4011 RN 00 | 45 | 0.6 |
| No layer (comparison) | | <0.1 |

We claim:

1. A hygienic absorbent pad which comprises an elongate absorbent core, a liquid pervious sheet over the front face of the absorbent core and a liquid impervious barrier sheet over the front face of the absorbent core and a liquid impervious barrier sheet over the back face of the absorbent core, which barrier sheet has longitudinal edge portions which cover the longitudinal sides of the absorbent core and an outer surface which faces away from the absorbent core wherein the outer surface of said longitudinal edge portions of the barrier sheet have a layer in contact therewith of a water absorbing polymer which is capable of inhibiting leakage of body fluids from the front surface of the absorbent pad to the sides thereof.

2. A hygienic absorbent pad according to claim 1 which is a sanitary towel in which the longitudinal edge portions of the barrier sheet cover the side margins at the front face of the absorbent core and the liquid pervious sheet surrounds the absorbent core and the barrier sheet.

3. A hygienic absorbent pad according to claim 1 in which the layer of water absorbing polymer is on the parts of the inner surface of the liquid pervious sheet which contact the longitudinal edge portions of the barrier sheet.

4. A hygienic absorbent pad according to claim 1 in which the layer of water absorbing polymer is in the form of a continuous strip.

5. A hygienic absorbent pad as claimed in claim 1 in which the water absorbing polymer has a water content when hydrated of 80% to 95% by weight.

6. A hygienic absorbent pad according to claim 1 in which the water absorbing polymer is a linear hydrophilic polyether polyurethane.

7. A method of forming a hygienic absorbent pad of claim 1 which comprises covering the front face of an elongate absorbent core with a liquid pervious sheet and covering the back face and the longitudinal sides of the absorbent core with a liquid impervious barrier sheet so that the longitudinal edge portions of the barrier sheet cover the longitudinal sides of the absorbent core characterised in that said longitudinal edge portions of the barrier sheet have a layer in contact with the outer surface thereof of a water absorbing polymer which is capable of inhibiting leakage of body fluids from the front surface of the absorbent pad to the sides thereof.

8. A linear hydrophilic polyurethane suitable for use as a water absorbing polymer in a hygienic absorbent pad of claim 1 wherein the linear hydrophilic polyurethane is thermoplastic and has a water content when hydrated of 80% to 95% by weight.

9. A linear hydrophilic polyurethane according to claim 8 which is derived from (a) polyethylene glycol of molecular weight 5000 to 10,000, (b) aliphatic diol, (c) water and (d) a di-isocyanate in which the molar ratio of (c) to (a) is less than 0.5:1, the molar ratio of (a) to (b) and (c) is 1:1.5 to 1:1 and the molar ratio of (d) to (a) and (b) and (c) is 0.9:1 to 1:1.

* * * * *